United States Patent
Ergler et al.

(10) Patent No.: US 10,088,578 B2
(45) Date of Patent: Oct. 2, 2018

(54) XRAY DETECTOR WITH ILLUMINATION LAYER ON CONVERTER ELEMENT

(71) Applicant: Siemens Healthcare GmbH, Erlangen (DE)

(72) Inventors: Thorsten Ergler, Erlangen (DE); Miguel Labayen De Inza, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/422,621

(22) Filed: Feb. 2, 2017

(65) Prior Publication Data

US 2017/0242135 A1    Aug. 24, 2017

(30) Foreign Application Priority Data

Feb. 18, 2016   (DE) .................. 10 2016 202 490

(51) Int. Cl.
| | |
|---|---|
| *G01T 1/24* | (2006.01) |
| *H01L 31/0224* | (2006.01) |
| *G01T 1/18* | (2006.01) |
| *A61B 6/00* | (2006.01) |

(52) U.S. Cl.
CPC ............ *G01T 1/241* (2013.01); *A61B 6/4241* (2013.01); *G01T 1/18* (2013.01); *H01L 31/0224* (2013.01)

(58) Field of Classification Search
CPC .................................. G01T 1/241; G01T 1/18
USPC .................................................. 250/370.12
See application file for complete search history.

(56) References Cited

U.S. PATENT DOCUMENTS

| | | | |
|---|---|---|---|
| 2008/0164418 A1* | 7/2008 | Shahar ...................... | G01T 1/24 250/370.01 |
| 2011/0253886 A1* | 10/2011 | Hackenschmied ..... | G01T 1/249 250/252.1 |
| 2015/0260856 A1 | 9/2015 | Dierre et al. | |

FOREIGN PATENT DOCUMENTS

| | | |
|---|---|---|
| DE | 102012213410 B3 | 9/2013 |
| WO | WO 2014132232 A2 | 9/2014 |

OTHER PUBLICATIONS

German Office Action dated Aug. 12, 2016.
German Decision to Grant and English translation thereof dated Feb. 23, 2017.
English translation of German Office Action dated Aug. 12, 2016.
Dr. Peter Sievers, DE-Forchheim; Dr. Stefan Wölfel, DE-Forchheim; Dr. Christian Schröter, DE-Forchheim: "Homogeneous sensor illumination using light guide,"Prior Art Journal #23, Nov. 24, 2014.

* cited by examiner

*Primary Examiner* — David Porta
*Assistant Examiner* — Meenakshi Sahu
(74) *Attorney, Agent, or Firm* — Harness, Dickey & Pierce, P.L.C.

(57) ABSTRACT

A counting x-ray detector includes, in a stack arrangement, a converter element for conversion of x-ray radiation into electrical charges and an electrode. The electrode is connected to the converter element electrically-conductively in a planar manner. The electrode is embodied at least partly transparently. The electrode includes the following layers: an electrically-conductive contact layer, an electrically-conductive first intermediate layer, an electrically-conductive high-voltage layer, and an illumination layer.

19 Claims, 5 Drawing Sheets

XRAY DETECTOR WITH ILLUMINATION LAYER ON CONVERTER ELEMENT

PRIORITY STATEMENT

The present application hereby claims priority under 35 U.S.C. § 119 to German patent application number DE 102016202490.6 filed Feb. 18, 2016, the entire contents of which are hereby incorporated herein by reference.

FIELD

At least one embodiment of the invention generally relates to a counting x-ray detector, a detector module, a medical device and/or a method for manufacturing a counting x-ray detector.

BACKGROUND

Counting, direct-converting x-ray detectors can be used in x-ray imaging, for example in computed tomography, angiography or radiography. The x-ray radiation or the photons can be converted into electrical pulses by a suitable sensor. Counting x-ray detectors make it possible, as well as counting events, also to provide information about the energy of the detected x-ray quantum. New opportunities are thus opened up in medical imaging for the analysis and evaluation of the signal.

CdTe, CZT, CdZnTeSe, CdTeSe, CdMnTe, InP, $TlBr_2$, $HgI_2$, GaAs or other materials can be used as converter material for the converter element for the sensor for example. The energy of the incident ionizing radiation is converted directly into electrical charges, so-called electron-hole pairs. A high voltage, for example for CdTe, CZT, CdZnTeSe, CdTeSe or CdMnTe in the range of −500 to −2000V, is applied to the converter element between an electrode as cathode and a readout contact as anode, in order to separate the charges of the electron-hole pairs released in the converter element. The high voltage is applied to the electrode via an external high-voltage source by way of an electrically-conductive contact. As a rule the sensor is connected in a planar manner in a stack arrangement to a readout unit and/or an evaluation unit, for example an integrated circuit (Application Specific Integrated Circuit, ASIC), via solder connections, electrically-conductive adhesive or other methods. The electrical pulses are evaluated by an evaluation unit, for example by an ASIC. The stack arrangement having the sensor and the integrated circuit is connected to a further substrate, for example a circuit board, a ceramic substrate such as HTCC or LTCC or others for example. The electrical connections for reading out the readout and/or the evaluation unit can be embodied by way of through silicon vias (TSV) or wire bonds.

A direct-converting x-ray radiation detector, which has at least one electrode attached to a semiconductor, is known from DE 10 2012 213 410 B3. The at least one electrode and the semiconductor are connected electrically-conductively, wherein the at least one electrode is embodied transparent and electrically-conductive. In order to optimize the x-ray radiation detection it is known to irradiate the semiconductor used for detection with an additional radiation for creating additional charge carriers. IR, UV or visible radiation is used as additional radiation for example.

The trend to larger detector facilities, especially to larger z extents, and the simultaneous cost competition with established detector technologies, for example indirect converting detectors, present the development of detector apparatuses with new challenges.

SUMMARY

Embodiments of the invention specify a counting x-ray detector, a detector module, a medical device and a method for manufacturing a counting x-ray detector, which make possible an illumination of the converter element via the electrode, which make possible a mechanically stable arrangement of an illumination layer with larger z extents and which make possible low-cost manufacturing.

At least one embodiment of the invention is directed to a counting x-ray detector; at least one embodiment of the invention is directed to a detector module; at least one embodiment of the invention is directed to a medical device and at least one embodiment of the invention is directed to a method for manufacturing a counting x-ray detector.

At least one embodiment of the invention relates to a counting x-ray detector, wherein the x-ray detector, in a stack arrangement, has a converter element for conversion of x-ray radiation into electrical charges and an electrode. The electrode is connected electrically-conductively to the converter element in a planar manner. The electrode is embodied at least partly transparent. The electrode has the following layers: An electrically-conductive contact layer, an electrically-conductive first intermediate layer, an electrically-conductive high-voltage layer, and an illumination layer.

At least one embodiment of the invention further relates to a detector module having at least one inventive x-ray detector. The detector module can have a plurality of inventive x-ray detectors. The detector module can include a mechanical holder for the at least one x-ray detector. Advantageously the detector module can be connected to a receiving facility for detector modules to form a detector facility. The illumination layer can be assigned to a single x-ray detector.

At least one embodiment of the invention further relates to a medical device having an inventive x-ray detector of at least one embodiment of the invention. The advantages of the embodiments of the inventive x-ray detector can be transferred to the medical device. Advantageously the imaging can be improved by way of the irradiation of a quantity of light onto the converter element, as well as being temporally and spatially stabilized.

At least one embodiment of the invention further relates to a method for manufacturing a counting x-ray detector having the steps: Provision of a flowable mold material and a converter element with contact layer attached thereto, injection molding of the mold material for manufacturing an illumination layer, attaching the high-voltage layer to the illumination layer, and electrically-conductive connection of the high-voltage layer to the contact layer.

BRIEF DESCRIPTION OF THE DRAWINGS

Example embodiments of the invention are explained below in greater detail with reference to drawings. In the drawings.

DETAILED DESCRIPTION OF THE EXAMPLE EMBODIMENTS

Figure 1:
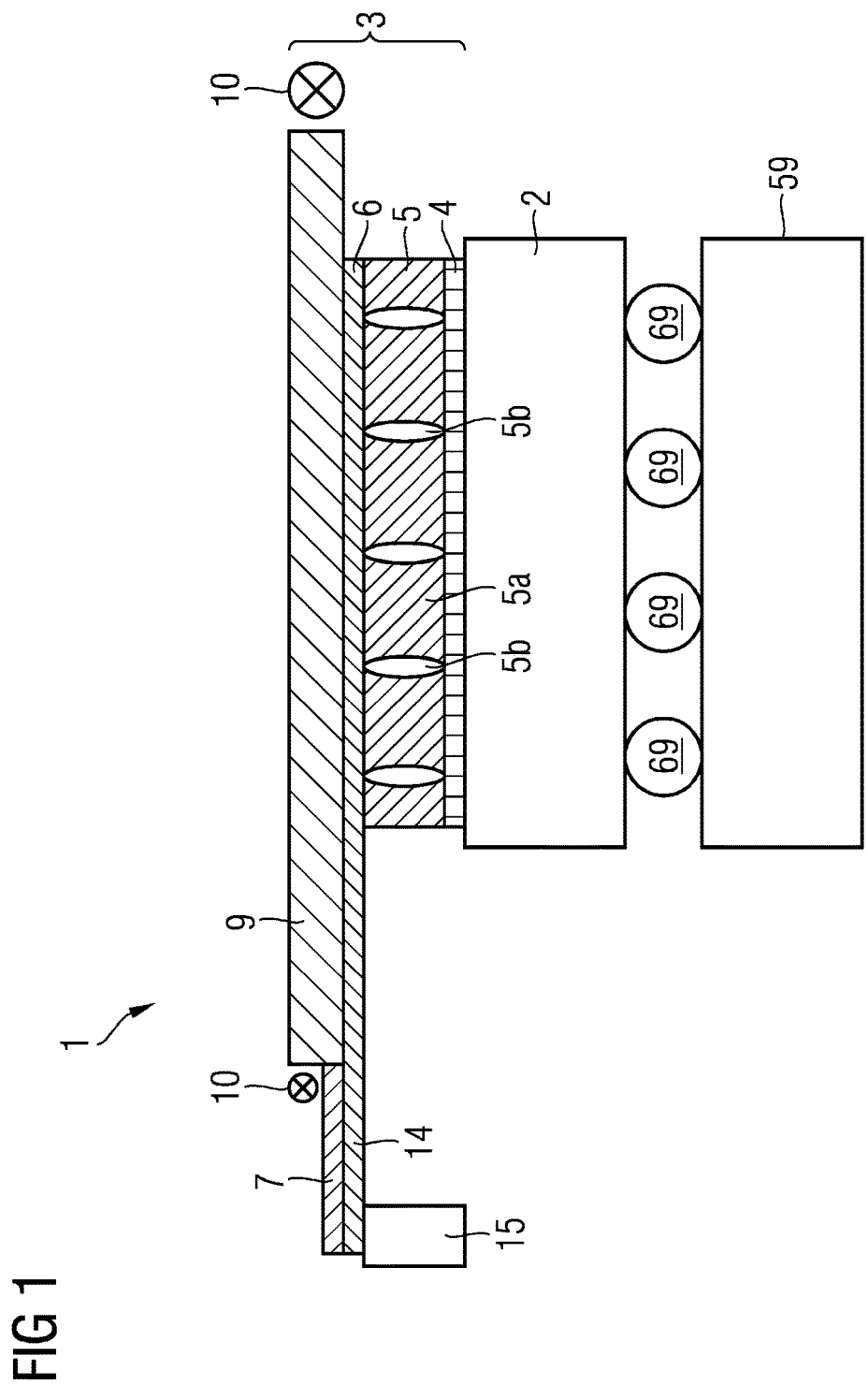
FIG. 1 shows a schematic concept of an inventive x-ray detector in accordance with a first form of embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a counting x-ray detector, wherein the x-ray detector, in a stack arrangement, has a converter element for conversion of x-ray radiation into electrical charges and an electrode. The electrode is connected electrically-conductively to the converter element in a planar manner. The electrode is embodied at least partly transparent. The electrode has the following layers: An electrically-conductive contact layer, an electrically-conductive first intermediate layer, an electrically-conductive high-voltage layer, and an illumination layer.

The inventors have recognized that a demand exists for an electrode for an x-ray detector, which is transparent or only slightly absorbent, for example for x-ray radiation, UV, IR or visible light, which is simultaneously easy to manufacture and which simultaneously irradiates a quantity of light onto the converter element. The inventors have further recognized that the illumination layer included in the electrode can exhibit a greater stability with greater extents, in particular greater z extents, of the x-ray detector or of a detector module. The inventors have recognized that it is possible to integrate the illumination layer into the electrode, to irradiate the converter element by way of the illumination layer included in the electrode with a quantity of light and to embody the electrode such that the converter element is able to be illuminated by the electrode. The illumination layer can in particular be a passive illumination layer.

Illumination layers that are included as a type of bridge over the x-ray detector or are included without being in direct mechanical connection with the x-ray detector, can have vibrations imparted to them or be deformed with rotations, especially above 5 Hz. The greater extent of the illumination layer can be associated with the spacing between the fastening points of the illumination layer becoming ever greater and thus deformations or vibrations being more likely to occur. The illumination layer can for example be fastened via fastening points to the module mechanics. The fastening points can be located at a greater spacing by comparison with the z extent of the x-ray detector or detector module. For detector modules with a z extent of more than 20 cm or more than 30 cm, with rotation speeds of more than 4 Hz, deformations can be caused during operation by the centrifugal forces. Any deformations of the illumination layer can disadvantageously lead to fluctuations in the illumination of the converter element.

The x-ray detector is a counting x-ray detector. The x-ray detector has a direct-converting converter element, for example CdTe, CZT, CdZnTeSe, CdTeSe, CdMnTe, InP, $TlBr_2$, $HgI_2$ or GaAs. The converter element and the readout and/or the evaluation electronics can be arranged in a stack arrangement. On the side of the converter element facing away from the radiation at least one readout contact can be provided as an anode. The anode can be subdivided in a pixilated manner. On the side of the converter element facing towards the radiation an electrode is provided as a cathode. The electrode is embodied in a planar manner. A sensor can include the converter element, the electrode and the anode.

The electrode and the converter element are arranged in a stack arrangement. The electrode and the converter element can be connected electrically-conductively to one another in a planar manner. The electrode and the converter element can have at least approximately the same planar extent.

The electrode is embodied at least partly transparent. The electrode can be at least partly transparent or be slightly absorbent, for example for x-ray radiation, UV, IR or visible light. Preferably the electrode can be at least partly transparent or be slightly absorbent for x-ray radiation and IR light. The electrode can be embodied at least partly transparent for UV, IR or visible light, so that maximum of 75 percent, preferably at most of 60 percent, further preferably at most of 50 percent and mostly preferably at most of 40 percent of the incident radiation of UV, IR or visible light can be absorbed. The electrode is at least partly transparent, so that a quantity of light can be irradiated in from the illumination layer onto the converter element and the intervening layers of the electrode have a quantity of light at least partly passing through them. The quantity of light coupled into the illumination layer can be greater than the quantity of light irradiated onto the converter element.

The electrode can be at least partly electrically-conductive. The following layers of the electrode can be at least partly connected electrically-conductively to one another: The electrically-conductive contact layer, the electrically-conductive first intermediate layer and the electrically-conductive high-voltage layer. The electrode has a number of layers in a stack arrangement. The layers can be connected to one another in a planar manner. The electrode can have the following layers in the following order: The electrically-conductive contact layer, the electrically-conductive first intermediate layer, the electrically-conductive high-voltage layer, and the illumination layer. The contact layer can be connected directly electrically-conductively to the converter element. The contact layer can be attached directly to the converter element. The first intermediate layer can be attached directly to the contact layer. The high-voltage layer can be attached directly to the first intermediate layer. The illumination layer can be attached directly to the high-voltage layer. Attachment can be understood as deposition, vapor deposition, gluing, application, attachment, brushing on or other methods for attaching layers.

The characteristics of the converter element for detection of ionizing radiation, for example x-ray radiation, can be optimized by irradiating in additional IR, UV or visible light, for example from the side facing towards the radiation. The electrode can be at least partly transparent for IR, UV or visible light and the x-ray detector can advantageously be optimized by way of additionally radiating in IR, UV or visible light.

The electrically-conductive contact layer can be a thin metallic layer, for example featuring platinum, indium, molybdenum, tungsten, ruthenium, rhodium, gold, silver or aluminum. The electrically-conductive contact layer can be a thin-film layer. The contact layer can be embodied at least partly transparent. The contact layer can have a thickness of maximum 250 nm, preferably of maximum 200 nm, especially preferably of maximum 150 nm. The contact layer can be embodied porous, wherein the pores of the contact layer are transparent for electromagnetic radiation, in particular IR and x-ray radiation. The contact layer can be embodied as a reticular layer.

The electrically-conductive first intermediate layer can be embodied at least partly transparent. The first intermediate layer can be an electrically-conductive adhesive tape. The electrically-conductive first intermediate layer can feature an electrically-conductive glue. The electrically-conductive first intermediate layer can feature an adhesive agent and at least one electrically-conductive filler element embedded therein. The adhesive agent can be embodied at least partly transparent or semi-transparent, preferably transparent, for electromagnetic radiation, in particular x-ray radiation and IR light. The filler element can form an electrically-conductive connection between the contact layer and the high-voltage layer. The filler element can be embodied from a metal. The first intermediate layer can have a degree of absorption of a maximum of 75 percent, preferably of a maximum of 60 percent, especially preferably of a maximum of 50 percent and mostly preferably of a maximum of 40 percent of the intensity of IR, UV or visible light.

The electrically-conductive high-voltage layer can be embodied as a TCO layer. The TCO layer can be embodied from at least one material of the following list: Indium tin oxide, indium oxide, tin oxide, zinc oxide, cadmium oxide, poly3,4-ethylenedioxythiphene, polystyrene sulfonate, carbon nano tubes or derivatives of polyaniline. The TCO layer can be embodied from at least one pure or one doped material.

The electrically-conductive high-voltage layer can be embodied in the shape of a grating. The electrically-conductive high-voltage layer can be embodied as an electrically-conductive grating, in particular as a metallic grating. The electrically-conductive grating can feature silver, nickel, gold or the like. The electrically-conductive grating can be embodied thin enough for the electrically-conductive grating to be transparent in relation to x-ray radiation. The electrically-conductive grating, in particular the webs of the electrically-conductive grating, can be embodied such that it is not transparent for UV, IR or visible light. The electrically-conductive grating can be embodied at least partly transparent for UV, IR or visible light, so that a maximum of 30 percent of the incident radiation of UV, IR or visible light is absorbed. The electrode can be embodied at least partly transparent for UV, IR or visible light, so that a maximum of 75 percent, preferably at most 60 percent, further preferably at most 50 percent and mostly preferably at most 40 percent, of the incident radiation of UV, IR or visible light can be absorbed. The electrically-conductive grating can form a regular or irregular pattern. The spacings between the webs of the grating can be sufficiently small for sufficiently many of the filler elements of the first intermediate layer to have electrically-conductive contact with the electrically-conductive grating.

The illumination layer can also be referred to as a light distributor layer. A quantity of light can be irradiated as evenly as possible onto the converter element by the illumination layer. The quantity of light emitted by the light source can be distributed by way of the illumination layer as evenly as possible over the planar extent of the converter element. The illumination layer can feature PET or another thermoplastic. The material of the illumination layer can have a melting point of more than 50° C. The material of the illumination layer can preferably not be deformed at temperatures of below 50° C., so that deformations of the illumination layer can be avoided during the operation of the x-ray detector for example. The illumination layer can be provided as a flowable material for manufacturing of the x-ray detector. The illumination layer can have a spatially even inner structure, for example thickness. The illumination layer can have a spatially different inner structure, for example thickness.

The illumination layer can be an optical waveguide or can be used as an optical waveguide, thus the illumination layer can have a greater z extent and an even incident radiation onto the converter element can be made possible. A quantity of light can be coupled out of the optical waveguide via a coupling-out structure.

The layer thickness of the illumination layer, of the high-voltage layer and of the first intermediate layer can be selected such that the electrode absorbs a maximum of 20 percent of the x-ray radiation. The layer thickness of the illumination layer, of the high-voltage layer and of the first intermediate layer can be selected such that the incident radiation of UV, IR or visible light varies by a maximum of 50 percent over the entire surface of the electrode or of the converter element. The layer thickness of the illumination layer, of the high-voltage layer and of the first intermediate layer can be selected such that the high-voltage layer and also the first intermediate layer absorb a maximum of 75 percent, preferably at most 60 percent, further preferably at most 50 percent and mostly preferably at most 40 percent of the incident radiation of UV, IR or visible light.

Through the planar mechanical connection of the illumination layer with another layer of the electrode, for example the high-voltage layer, the carrier protection layer or the second intermediate layer, the illumination layer is also connected to the converter element in a planar manner, at least indirectly by way of the other layers of the electrode. Advantageously the unit comprising converter element and electrode can exhibit an increased stability against deformations during rotations 3 Hz to 5 Hz, preferably of more than 5 Hz, especially preferably of up to 10 Hz. In particular the unit comprising converter element and electrode can exhibit an increased stability against deformations during rotations for greater z extents. Advantageously temporal and spatial fluctuations of the quantity of light radiated in onto the converter element can be reduced by way of the increased stability. With illumination layers that are not connected mechanically to the converter element in a planar manner, temporal and spatial fluctuations of the quantity of light radiated in onto the converter element can be conditional on deformations during rotations. Advantageously the quantity of light radiated in onto the converter element can be stabilized temporally and spatially, so that a stable operation of the x-ray detector can be achieved by way of the illumination of the converter element. The electrode can be stable as regards torsions of deformations. The electrode can be stiff. Advantageously the electrode can be mechanically stable in relation to deformations, caused for example by centrifugal forces during rotations of the x-ray detector around a point.

In the direction of incident x-ray radiation of the electrode an anti-scatter grid without direct mechanical connection can be provided, in order to reduce the incidence of scattered x-ray photons striking the converter element.

Advantageously the illumination layer and the high-voltage layer can be included in the electrode. Advantageously the electrode can be connected in a planar mechanical connection to the converter element. Advantageously, through the use of the inventive electrode, fewer production steps or installation steps are needed for manufacturing the x-ray detector. Advantageously production costs can be reduced. Advantageously the electrode can be released at least partly from the converter element, for example by separation between the contact layer and the high-voltage layer. The first intermediate layer can be carefully removed, by pulling it away for example, for at least partial release of the electrode from the converter element. Advantageously the high-voltage layer and the illumination layer, for example in the event of a defect, can be exchanged.

In accordance with an embodiment of the invention, the illumination layer is manufactured by way of an injection molding method. The illumination layer can comprise an illumination element. In particular the illumination layer can comprise an illumination element that is manufactured by way of an injection molding method. The illumination layer or the illumination element can be delimited in three spatial dimensions. Advantageously the illumination layer can be manufactured as an exact fit for the x-ray detector or the detector module. Advantageously coupling-out structures can be manufactured during the injection molding method.

In accordance with an embodiment of the invention the electrode further has a carrier protection layer arranged between the high-voltage layer and the illumination layer.

The carrier protection layer can be a carrier film. The carrier protection layer can be embodied for example from polyethylene terephthalate, polyethylene terephthalate-glycol, polypropylene, polyethylene, polyvinylchloride or the like. The carrier protection layer can be embodied electrically insulating or non-conductive. The carrier protection layer can be attached directly to the high-voltage layer. Advantageously the high-voltage layer can be attached to the carrier protection layer. Advantageously manufacturing can be simplified. Advantageously the carrier protection layer can be used with the high-voltage layer as a delimiting layer in the injection molding method.

In accordance with an embodiment of the invention the electrode further has a second intermediate layer arranged between the high-voltage layer and the illumination layer.

The second intermediate layer can be electrically conductive. The second intermediate layer can be electrically insulating or non conductive. The second intermediate layer can preferably be electrically insulating. The second intermediate layer can be an adhesive tape or feature a glue. The second intermediate layer can be embodied the same as the first intermediate layer. The second intermediate layer can feature an adhesive agent. The second intermediate layer can have at least one electrically-conductive filler element embedded in the adhesive agent. The second intermediate layer can be attached directly to the high-voltage layer. Advantageously, for mechanical connection of the high-voltage layer or of the carrier protection layer, the second intermediate layer can be used with the illumination layer. Advantageously the second intermediate layer can establish an adhesive connection between the high-voltage layer or the carrier protection layer and the illumination layer. The illumination layer can be manufactured in an injection molding method and subsequently advantageously by way of the second intermediate layer, be mechanically connected to a carrier protection layer attached in any way to the high-voltage layer. Advantageously manufacturing can be simplified.

According to an embodiment of the invention, the x-ray detector further has a continuation or elongation of the high-voltage layer as an electrically-conductive connection to a voltage source. The electrically-conductive connection can be embodied as a continuation of the high-voltage layer. In this case the high-voltage layer extends beyond the extent of the illumination layer or of the converter element. For example a continuation can be embodied in the form of a narrow band, wherein the high-voltage layer can be longer in one direction than a side of the stack structure, of the illumination layer or of the converter element and wherein the high-voltage layer in the area of the continuation, can be narrower than another side of the stack structure, of the illumination layer or of the converter element. The electrically-conductive connection can include the first carrier protection layer. The continuation of the high-voltage layer can be covered partly or completely by the possible first carrier protection layer. Advantageously the first carrier protection layer can have an electrically-insulating or mechanical support function. Advantageously the voltage source can be connected to a connection point, for example a solder connection, or a few connection points can be connected to the high-voltage layer. Advantageously a suitable mechanical stability of the electrically-conductive connection between the voltage source and the electrode or the high-voltage layer can be guaranteed. Advantageously the electrically-conductive connection or the continuation of the high-voltage layer can be manufactured jointly with the continuation of the carrier protection layer in one manufacturing step.

According to an embodiment of the invention, the x-ray detector further has a light source for coupling a quantity of light into the illumination layer. The x-ray detector can have the light source in a lateral arrangement to the electrode. The x-ray detector can have a number of light sources in a lateral arrangement to the electrode, for example distributed evenly along the circumference and/or on a number of sides of the electrode. The light source can be arranged such that a quantity of light is able to be coupled into the illumination layer. The light source can be in mechanical contact with the illumination layer. The light source can be included in the illumination layer, for example an LED can be let into the illumination layer with the aid of a recess in the layer. Advantageously can a quantity of light emitted by the light source can be coupled as completely as possible into the illumination layer. Reflectors can be arranged for optimizing the coupling in of the quantity of light. The wavelength of the light source can preferably lie in the range of the visible or infrared light. The wavelength of the light source can lie in the range of 400 nm to 780 nm.

According to an embodiment of the invention, a quantity of light irradiated in by the illumination layer by way of a coupling-out structure onto the converter element varies within an illuminated surface of the converter element by less than 50 percent.

The coupling-out structure can be provided on the upper side, the side facing away from the converter element, or the lower side, the side facing towards the converter element, of the illumination layer. The coupling-out structure can be included in the illumination layer. The coupling-out structure can be embodied as raised areas or depressions. The coupling-out structure can be attached to the illumination layer. The coupling-out structure can be embodied for example as a metallic grating. The coupling-out structure can be included in the high-voltage layer adjoining the illumination layer or can be embodied by the adjoining high-voltage layer. The coupling-out structure can be embodied in the shape of a grating or in a reticular shape. The coupling-out structure can be provided in an even or uneven pattern. The coupling-out structure can be different depending on the location, in particular can have different spatial densities of at least local refractive index transitions. The coupling-out structures can in particular be larger or become larger when spatially more closely adjacent to the light source or spaced further away from it. The coupling-out structures can lead to an at least local refractive index transition.

The coupling-out structure can be embodied such that the quantity of light from the illumination layer is irradiated in evenly onto the converter element, for example over a thickness adapted across the surface of at least local index of refraction transitions. The coupling-out structure can advantageously be manufactured with only slight deviations over the surface of the illumination layer. The coupling-out structures can at least locally reduce the total reflection of the IR, UV or visible light. The coupling-out structure can guarantee a planar, spatially even irradiation of their quantity of light onto the converter element. Advantageously the converter element can be illuminated spatially evenly. Advantageously the x-ray detector can be optimized advantageously with the aid of the irradiation of the quantity of light.

According to an embodiment of the invention, the electrode absorbs less than 30 percent of the x-ray radiation irradiated onto the converter element. The electrode can be embodied such that the materials used do not exceed a limited absorption coefficient, so that less than 30 percent of the x-ray radiation irradiated onto the converter element can be absorbed by the electrode. The thicknesses of the layers of the electrode can be selected such that less than 30 percent of the x-ray radiation irradiated onto the converter element can be absorbed by the electrode. The structures of the layers of the electrode can be embodied such that less than 30 percent of the x-ray radiation irradiated onto the converter element can be absorbed by the electrode, for example the contact layer or the high-voltage layer can be embodied as a type of net or grating. The aforementioned measures to limit the absorption of x-ray radiation can be advantageously combined with one another. Advantageously the influence of the electrode on the imaging characteristics of the x-ray detector can be reduced.

At least one embodiment of the invention further relates to a detector module having at least one inventive x-ray detector. The detector module can have a plurality of inventive x-ray detectors. The detector module can include a mechanical holder for the at least one x-ray detector. Advantageously the detector module can be connected to a receiving facility for detector modules to form a detector facility. The illumination layer can be assigned to a single x-ray detector.

According to an embodiment of the invention an illumination layer is assigned to a plurality of x-ray detectors. The illumination layer can be assigned to all x-ray detectors of the detector module. The illumination layer can be assigned to a part of the x-ray detectors of the detector module. The illumination layer can be exclusively assigned to the x-ray detectors of the detector module. The assignment can be understood as spanning or coverage. The illumination layer can be assigned to the x-ray detectors of a number of detector modules. The illumination layer can be assigned to the x-ray detectors of all detector modules of a detector facility. Advantageously the light source can be arranged to the side of the electrode at the edge of the detector module.

Advantageously a separate light source or illumination layer can be avoided for x-ray detectors arranged in the middle of the detector module.

According to an embodiment of the invention at least two x-ray detectors are arranged at an angle to one another. The x-ray detectors can be arranged within the detector modules such that their surface normal is not parallel. For example in the z direction, the direction of rotation of a computed tomograph, x-ray detectors further away from the isocenter are inclined such that their surface normal encloses an angle greater than 0 degrees to the surface normal of a central x-ray detector closer to the isocenter.

The x-ray detectors can be arranged within the detector facility such that their surface normal is not parallel. For example the x-ray detectors further away from the isocenter in the phi direction, which specifies the angle between the central ray through the isocenter and the ray at an angle phi in relation to the isocenter, can be inclined such that their surface normals enclose an angle greater than 0 degrees to the surface normal of a central x-ray detector closer to the isocenter. For example the receiving facility for detector modules can be in the shape of an arc along the phi direction and/or the z direction.

Advantageously the x-rays emitted by a radiation source can strike the converter element at least approximately in parallel to the surface normal of the x-ray detector. The illumination layer can follow the contour of the x-ray detectors or the surface of the converter element. The illumination layer can lie on the converter element in a planar manner. The illumination layer can lie continuously on the converter element of a number of detectors. The shape of the illumination layer can be embodied in accordance with the arrangement of the x-ray detectors. The x-ray detector or a number of x-ray detectors can, in particular for greater z coverage, be inclined in the direction of the point radiation source.

At least one embodiment of the invention further relates to a medical device having an inventive x-ray detector of at least one embodiment of the invention. The advantages of the embodiments of the inventive x-ray detector can be transferred to the medical device. Advantageously the imaging can be improved by way of the irradiation of a quantity of light onto the converter element, as well as being temporally and spatially stabilized.

According to an embodiment of the invention the medical device has an inventive detector module. The advantages of the embodiments of the inventive detector module can be transferred to the medical device. Advantageously the imaging can be improved by way of the irradiation of a quantity of light onto the converter element, as well as being temporally and spatially stabilized. In particular the medical device can be a computed tomograph. Especially advantageous is the use of embodiments of the inventive detector module for detector facilities that are spread out in the phi direction and the z direction. Especially advantageous is the use of the inventive detector module for greater z extents of for example at least 3 cm, preferably at least 5 cm, especially preferably at least 7 cm.

At least one embodiment of the invention further relates to a method for manufacturing a counting x-ray detector having the steps: Provision of a flowable mold material and a converter element with contact layer attached thereto, injection molding of the mold material for manufacturing an illumination layer, attaching the high-voltage layer to the illumination layer, and electrically-conductive connection of the high-voltage layer to the contact layer.

The inventors have recognized that the high-voltage layer in conjunction with the illumination layer is able to be manufactured as a common component. An injection molding method can be employed in particular in this case, for example at least for manufacturing the high-voltage layer. The high-voltage layer, for example additionally in conjunction with a carrier protection layer, can be used in this case as delimitation of the illumination layer in the injection molding method. The common component having the high-voltage layer and the illumination layer can subsequently, for example by way of a first intermediate layer, be connected to the contact layer on the surface of the converter element.

The high-voltage layer can for example be laid in the mold in conjunction with a PET film and/or the carrier protection layer and be used as delimitation of the illumination layer in the injection molding method. The mold material can be attached to the high-voltage layer, possibly in conjunction with PET film and/or carrier protection layer, wherein the illumination layer is produced. high-voltage layer and illumination layer can be included in one component.

The illumination layer can be manufactured via an injection molding method. The high-voltage layer can be attached directly to the illumination layer by way of vapor deposition, sputter methods or galvanization. The high-voltage layer, for example also in conjunction with a carrier protection layer, can be attached to the illumination layer via a gluing method.

In the step of provision of a flowable material and of a converter element with attached contact layer the initial products of the x-ray detector are provided. The flowable mold material can be present for example as powder, granulate, melt or paste. The flowable mold material can feature PET or another thermoplastic. The mold material can have a melting point of more than 50° C., preferably of more than 60° C. and especially preferably of more than 70° C. The material of the illumination layer can include the mold material or can feature the mold material. A contact layer is attached to a surface of the converter element. The contact layer is a layer of the electrode. The contact layer can be provided prepared in such a way that the contact layer is prepared for planar attachment of the further layers.

The illumination layer is manufactured in the step of injection molding the mold material. A mold can be provided. The flowable mold material can be poured into the mold by way of a worm or under pressure. The mold is embodied such that the illumination layer can be manufactured advantageously to be an exact fit for the x-ray detector, for the detector module or for the detector facility, for example according to the arrangement of x-ray detectors at an angle to one another. The illumination layer can include an illumination element.

The illumination layer or the illumination element can be delimited in three spatial directions. The mold can define the three-dimensional delimitation of the illumination layer or of the illumination element. The mold can be embodied in such a way that the illumination element has smooth outer surfaces. The mold can be embodied in such a way that the illumination layer has coupling-out structures, for example on the side facing towards or away from the converter element. The coupling-out structures can be embodied as raised areas or depressions. The mold can be embodied in such a way that a facility for installing the light source in or on the illumination layer is provided. The installation facility can be embodied as an especially exact-fit cutout for the light source. Advantageously coupling-out structures can be manufactured during the injection molding method. The step of injection molding can have further steps, for example cooling off, hardening and finishing. After the injection molding steps the illumination layer can be available as a rigid component for further processing. The illumination layer can be available without an inner structure, for example bubbles or voids.

In the step of attaching the high-voltage layer to the illumination layer a connection is established between the high-voltage layer and the illumination layer, at least indirectly via further layers or directly. The electrically-conductive grating can be attached directly to the illumination layer during manufacturing for example via vapor deposition, sputter methods or galvanization. The high-voltage layer can be attached to the illumination layer by way of a second intermediate layer and possibly a carrier protection layer. The attachment step can be included in the injection molding step. The high-voltage layer can for example be laid in the mold in conjunction with a PET film and/or the carrier protection layer and used as a delimitation of the illumination layer in the injection molding method.

In the step of electrically-conductively connecting the high-voltage layer to the contact layer, an electrically-conductive connection is established between the contact layer and the high-voltage layer. The first intermediate layer is used to connect the layers. The first intermediate layer establishes an electrically-conductive connection and a mechanical connection between the contact layer and the high-voltage layer. Bubbles, especially air bubbles between the contact layer and the high-voltage layer, can be avoided by even pressure on the illumination layer and the layers connected thereto during the connection process. In the connection step the temperature can be adapted to the optimum temperature range of the adhesive agent of the first intermediate layer. Smaller differences in height, for example in the range of up to 20 µm, can be compensated for by way of the first intermediate layer, for example by the layer thickness of the first intermediate layer.

Advantageously, with the aid of the injection molding method, an optimum shape of the illumination layer in accordance with the arrangement of the x-ray detectors can be achieved. Advantageously, with the aid of the second intermediate layer the high-voltage layer and the illumination layer can be attached to the contact layer attached to the converter element.

FIG. 1 shows an example form of embodiment of the inventive x-ray detector 1 in accordance with a first form of embodiment. The x-ray detector 1 has, in a stack arrangement, a converter element 2 for conversion of x-ray radiation into electrical charges and an electrode 3. The electrode 3 is connected electrically-conductively to the converter element 2 in a planar manner. The electrode 3 is embodied at least partly transparent. The electrode 3 has the following layers: An electrically-conductive contact layer 4, an electrically-conductive first intermediate layer 5, an electrically-conductive high-voltage layer 6, and an illumination layer 9.

The x-ray detector 1 further has solder connections 69 to the readout and/or evaluation unit 59. The solder connection 69 can be embodied as a solder bump, stub bumps or a copper pillar or as an electrically-conductive adhesive. The x-ray detector 1 further has light sources 10 attached to the side of the illumination layer 9, which are arranged such that a quantity of light can be coupled into the illumination layer 9. The x-ray detector 1 further has a continuation of the high-voltage layer 6, wherein a carrier protection layer 7 is attached to the continuation. The continuation of the high-voltage layer 6 is an electrically-conductive connection 14 to the voltage source 15. The electrically-conductive connection 14 is connected electrically-conductively via a solder connection or an indirect connection to the voltage source 15. The incident direction of the x-ray radiation corresponds in FIG. 1 to the direction from top to bottom. The x-ray radiation can first strike the illumination layer 9.

The electrode 3 and the converter element 2 can at least approximately have the same planar extent. The illumination layer 9 can have a greater planar extent than the other layers of the electrode 3, for example for holding a facility for coupling-in a quantity of light of the light source 10.

The electrode 3 is embodied at least partly transparent. The electrode 3 is embodied at least partly transparent for UV, IR or visible light, so that a maximum of 75 percent, preferably at most 60 percent, further preferably at most 50 percent and mostly preferably at most 40 percent of the irradiation of UV, IR or visible light can be absorbed. The electrode 3 is at least partly transparent, so that a quantity of light can be irradiated in from the illumination layer 9 to the converter element 2 and the layers of the electrode 3 lying therebetween will be at least partly penetrated by a quantity of light. The quantity of light coupled into the illumination layer 9 can be greater than the quantity of light irradiated onto the converter element 2.

The electrode 3 is at least partly electrically-conductive. The following layers of the electrode 3 can be connected at least partly electrically-conductively with one another: The electrically-conductive contact layer 4, the electrically-conductive first intermediate layer 5 and the electrically-conductive high-voltage layer 6. The electrode 3 has a number of layers in a stack arrangement. The layers have a planar connection with one another. The electrode 3 has the following layers in the following order: The electrically-conductive contact layer 4, the electrically-conductive first intermediate layer 5, the electrically-conductive high-voltage layer 6, and the illumination layer 9. The contact layer 4 is connected directly electrically-conductively to the converter element 2. The contact layer 4 is attached directly to the converter element 2. The first intermediate layer 5 is attached directly to the contact layer 4. The high-voltage layer 6 is attached directly to the first intermediate layer 5. The illumination layer 9 is attached directly to the high-voltage layer 6.

The electrically-conductive contact layer 4 is a thin metallic layer, for example featuring platinum, indium, molybdenum, tungsten, ruthenium, rhodium, gold, silver or aluminum. The electrically-conductive contact layer 4 is a thin-film layer. The contact layer 4 is embodied at least partly transparent. The contact layer 4 has a thickness of maximum 250 nm, preferably maximum 200 nm, especially preferably maximum 150 nm. The contact layer 4 is embodied porous or as a reticular layer.

The electrically-conductive first intermediate layer 5 is embodied at least partly transparent. The first intermediate layer 5 is an electrically-conductive adhesive tape or features an electrically-conductive adhesive. The electrically-conductive first intermediate layer 5 has an adhesive agent 5a and at least one electrically-conductive filler element 5b embedded therein. The adhesive agent 5a is embodied at least partly transparent or semi-transparent, preferably transparent, for electromagnetic radiation, in particular x-ray radiation and IR light. The filler element 5b can form an electrically-conductive connection between the contact layer 4 and the high-voltage layer 6. The filler element 5b is embodied from a metal. The first intermediate layer 5 exhibits a degree of absorption of maximum 75 percent, preferably maximum 60 percent, especially preferably maximum 50 percent and mostly preferably maximum 40 percent of the intensity of IR, UV or visible light.

The electrically-conductive high-voltage layer 6 is embodied as a TCO layer or in the form of a grating, in particular as a metallic grating. The TCO layer is embodied from at least one material of the following list: Indium tin oxide, indium oxide, tin oxide, zinc oxide, cadmium oxide, poly3,4-ethylenedioxythiphene, polystyrene sulfonate, carbon nano tubes or derivates of polyaniline. The TCO layer is embodied from at least one pure or one doped material. The electrically-conductive grating has copper, silver, nickel, gold or the like. The electrically-conductive grating is embodied at least partly transparent for UV, IR or visible light, so that maximum 30 percent of the irradiation of UV, IR or visible light will be absorbed.

The quantity of light emitted by the light source 10 is at least partly distributed by way of the illumination layer 9 as evenly as possible over the planar extent of the converter element 2. The illumination layer 9 features PET or another thermoplastic. The material of the illumination layer 9 has a melting point of more than 50° C.

The layer thicknesses of the illumination layer 9, of the high-voltage layer 6 and of the first intermediate layer 5 are selected so that the electrode absorbs a maximum of 20 percent of the x-ray radiation. The layer thicknesses of the illumination layer 9, of the high-voltage layer 6 and of the first intermediate layer 5 are selected so that the irradiation of UV, IR or visible light varies by at most 50 percent over the entire surface of the electrode 3 or of the converter element 2. The layer thickness of the illumination layer 9, of the high-voltage layer 6 and of the first intermediate layer 5 is selected so that the illumination layer 9, the high-voltage layer 6 and also the first intermediate layer 5 absorb a maximum of 75 percent, preferably at most 60 percent, further preferably at most 50 percent and mostly preferably at most 40 percent of the irradiation of UV, IR or visible light.

Figure 2:
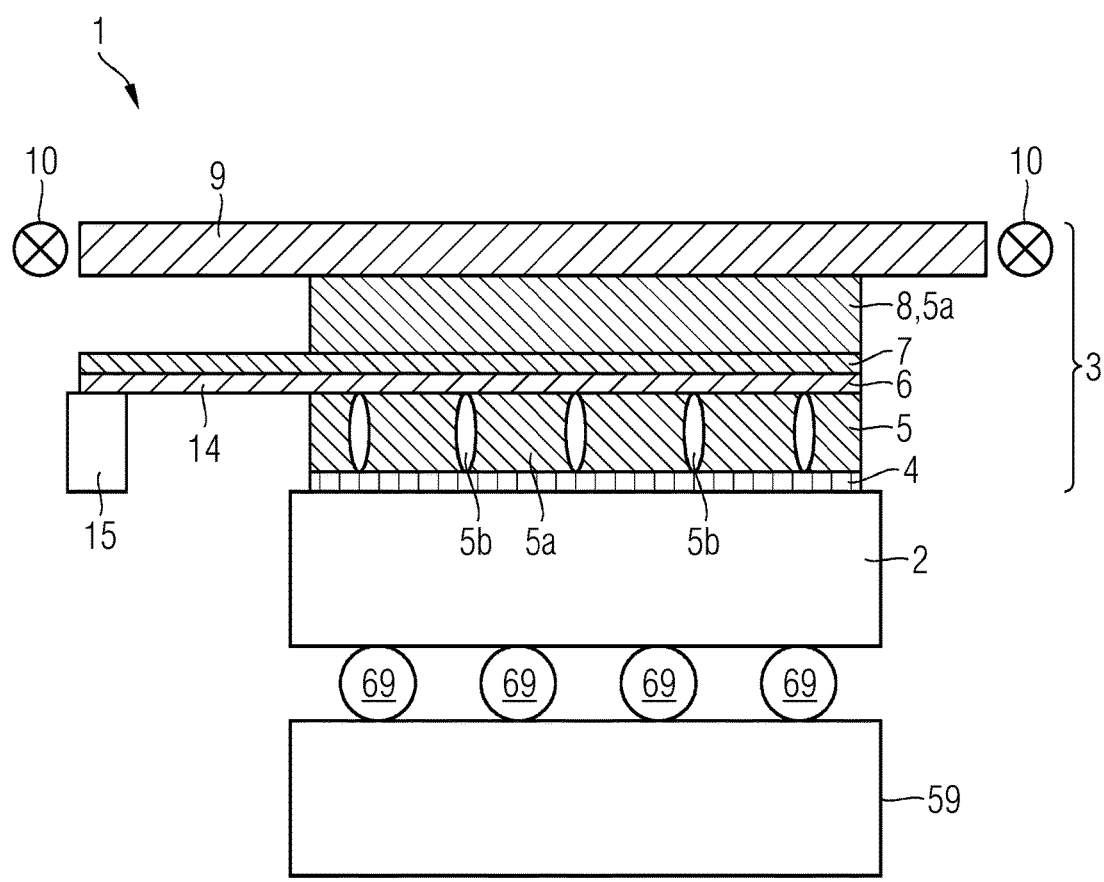
FIG. 2 shows a schematic concept of an inventive x-ray detector in accordance with a second form of embodiment.

FIG. 2 shows an example form of embodiment of the inventive x-ray detector 1 in accordance with a second form of embodiment. The x-ray detector 1 further has a carrier protection layer 7 and a second intermediate layer 8. The carrier protection layer 7 is a carrier film. The carrier protection layer 7 is embodied for example from polyethylene terephthalate, polyethylene terephthalate glycols, polypropylene, polyethylene, polyvinylchloride or the like. The carrier protection layer 7 is attached directly to the high-voltage layer 6. The second intermediate layer 8 is an adhesive tape or features a glue. The second intermediate layer 8 has an adhesive agent 5a. The second intermediate layer 8 is attached directly to the carrier protection layer 7. The second intermediate layer 8 is attached directly to the illumination layer 9. The x-ray detector 1 further has a continuation of the carrier protection layer 7, which is attached directly to the high-voltage layer 6.

Figure 3:
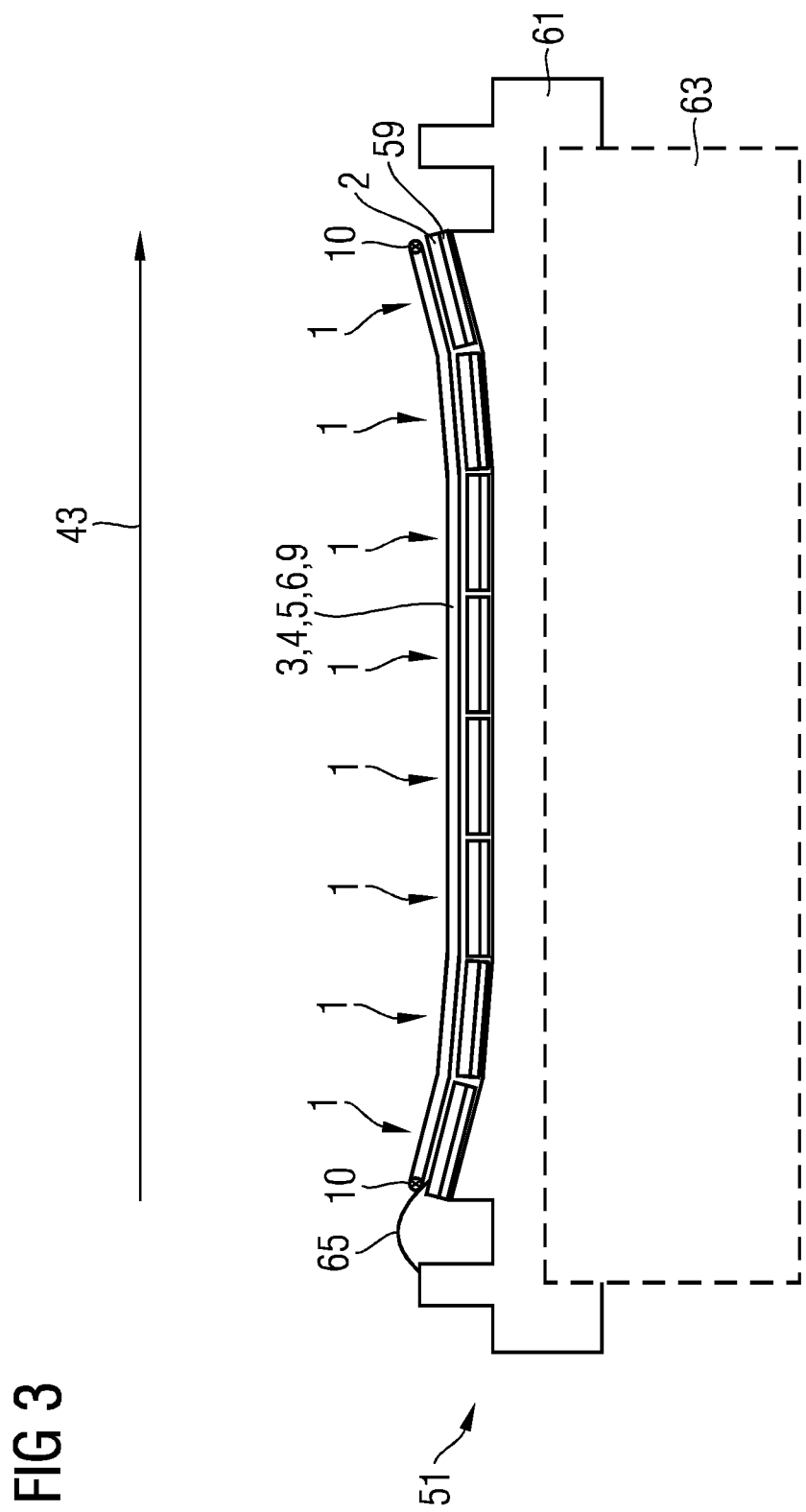
FIG. 3 shows a schematic concept of an embodiment of an inventive detector module.

FIG. 3 shows an example form of embodiment of the inventive detector module 51. The detector module 51 has a number of x-ray detectors 1, for example 8 x-ray detectors 1. The x-ray detectors 1 are mechanically connected to the module mechanics 61. The x-ray detectors 1 have an electrically-conductive connection to the module electronics 63. The module electronics 63 has a mechanical connection to the module mechanics 61. The x-ray detectors 1 are partly arranged at an angle not equal to 0 degrees in relation to one another, wherein the surface normals of neighboring x-ray detectors 1 enclose an angle not equal to 0 degrees. The illumination layer 9 is surrounded by the electrode 3. The illumination layer 9 is adapted to the arrangement of the x-ray detectors 1. The light sources 10 are arranged to the side of the illumination layer 9, so that a quantity of light is coupled into the illumination layer 9. The light sources 10 have an electrically-conductive connection 65 to a further voltage source.

Figure 4:
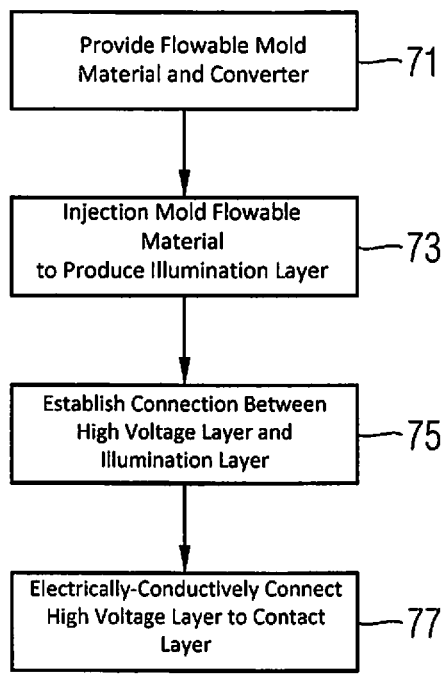
FIG. 4 shows a schematic diagram of an inventive method in accordance with a first form of embodiment.

FIG. 4 shows an example form of embodiment of the inventive method in accordance with a first form of embodiment. The method for manufacturing a counting x-ray detector has the steps provision 71, injection molding 73, attachment 75 and electrically-conductive connection 77.

The illumination layer is manufactured via an injection molding method. In the provision step 71 of a flowable mold material and a converter element with attached contact layer the initial products of the x-ray detector are provided. The flowable mold material is present for example as powder, granulate, melt or paste. The flowable mold material is PET or another thermoplastic. The mold material has a melting point of more than 50° C., preferably of more than 60° C. and especially preferably of more than 70° C. The material of the illumination layer consists of the mold material or includes the mold material. A contact layer is attached to a surface of the converter element. The contact layer is a layer of the electrode. The contact layer is provided prepared in such a way that the contact layer is prepared for planar attachment of the further layers.

In the step of injection molding of the mold material 73 the illumination layer is manufactured. A mold is provided. The flowable mold material is poured by way of a worm or under pressure into the mold. The mold is embodied such that the illumination layer is advantageously manufactured to fit the x-ray detector, the detector module or the detector apparatus exactly, for example in accordance with the arrangement of x-ray detectors at an angle to one another. The illumination layer is restricted in three spatial dimensions. The mold can define the three-dimensional restriction of the illumination layer. The mold is embodied such that the illumination element has smooth outer surfaces. The mold can be embodied such that the illumination layer has coupling-out structures, for example on the side facing towards or away from the converter element. The coupling-out structures can be embodied as raised areas or depressions. The mold can be embodied such that a facility for mounting the light source in or on the illumination layer is provided. The mounting facility can be embodied especially as an exact-fit recess for the light source. The injection molding step 73 can have further steps, for example cooling off, hardening and finishing. After the injection molding step 73 the illumination layer can be present as a rigid component for further processing. The illumination layer can be present without an inner structure, for example bubbles or voids.

In the step of attaching the high-voltage layer to the illumination layer 75 a connection is established between the high-voltage layer and the illumination layer, at least indirectly via further layers or directly. The electrically-conductive grating can be attached directly to the illumination layer during manufacturing for example via vapor deposition, sputter methods or galvanization. The high-voltage layer can be attached to the illumination layer by way of a second intermediate layer and any possible carrier protection layer. The high-voltage layer can be embodied as a coupling-out structure. The high-voltage layer can be attached directly to the illumination layer via vapor deposition, sputter methods or galvanization. The high-voltage layer, for example also in conjunction with a carrier protection layer, can be attached to the illumination layer via a gluing method.

In the step of electrically-conductively connecting the high-voltage layer to the contact layer 77 an electrically-conductive connection is established between the contact layer and the high-voltage layer. The first intermediate layer is used for the connection. The first intermediate layer establishes an electrically-conductive connection and a mechanical connection between the contact layer and the high-voltage layer. Bubbles, especially air bubbles, between the contact layer and the high-voltage layer can be avoided by an even pressure on the illumination layer and the layers connected thereto during the connection. In the connection step 77 the temperature can be adapted to the optimum temperature range of the adhesive agent of the first intermediate layer. Small differences in height, for example in the range of up to 20 µm, can be compensated for by way of the first intermediate layer, for example by the layer thickness of the first intermediate layer.

Figure 5:
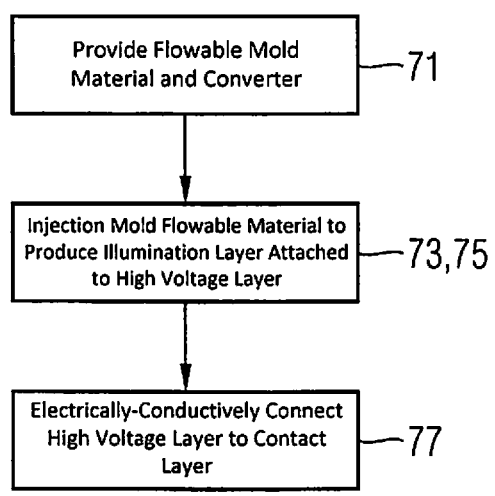
FIG. 5 shows a schematic diagram of an inventive method in accordance with a second form of embodiment.

FIG. 5 shows an example form of embodiment of the inventive method in accordance with a second form of embodiment. The attachment step 75 can be included in the injection molding step 73. The high-voltage layer can for example be laid into the mold in conjunction with a PET film and/or the carrier protection layer and used as the delimitation of the illumination layer in the injection molding method. The mold material can be attached to the high-voltage layer, possibly in conjunction with PET film and/or carrier protection layer, wherein the illumination layer is produced. High-voltage layer and illumination layer can be included in one component.

Figure 6:
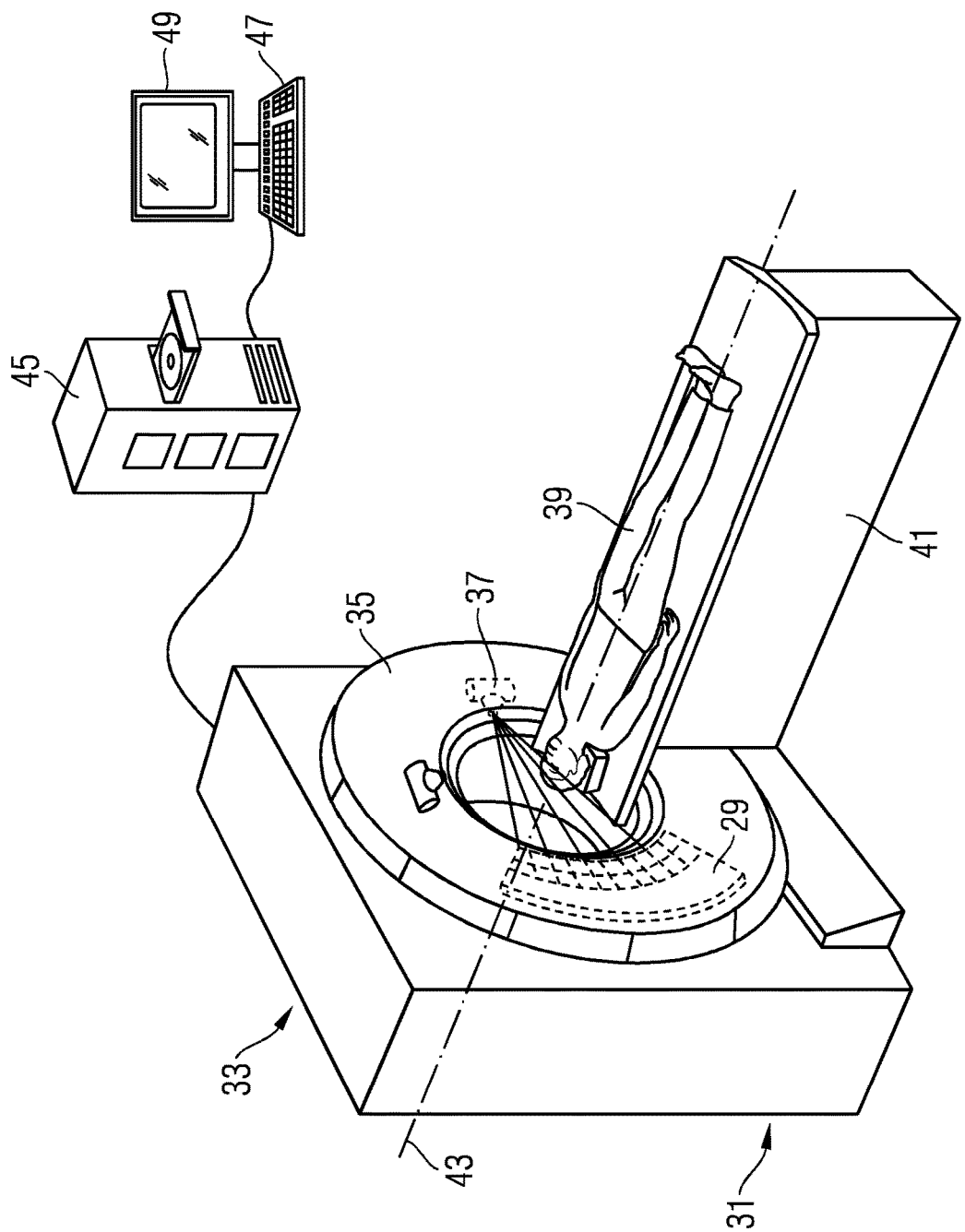
FIG. 6 shows a schematic diagram of an embodiment of an inventive computed tomograph.

FIG. 6 shows an example form of embodiment of the inventive computed tomograph 31 with a detector facility 29. The detector facility 29 features an embodiment of the inventive x-ray detector. The detector facility 29 can feature a number of detector modules that have at least one x-ray detector. Preferably the detector modules 51 feature a plurality of x-ray detectors in a two-dimensional matrix or arrangement. The computed tomograph 31 contains a gantry 33 with a rotor 35. The rotor 35 includes an x-ray source 37 and an embodiment of the inventive detector facility 29. The patient 39 is supported on the patient couch 41 and is able to be moved along the axis of rotation z 43 through the gantry 33. A processing unit 45 is used for control and processing of the slice images. An input facility 47 and an output facility 49 are connected to the processing unit 45.

Although the invention has been illustrated and described in greater detail by the preferred example embodiment, the invention is not however restricted by the disclosed examples and other variations can be derived herefrom by the person skilled in the art, without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A counting x-ray detector including, in a stack arrangement, a converter element for conversion of x-ray radiation into electrical charges and an electrode, the electrode being connected electrically-conductively to the converter element in a planar manner and the electrode being embodied at least partly transparent, the electrode including:
   an electrically-conductive contact layer,
   an electrically-conductive first intermediate layer,
   an electrically-conductive high-voltage layer, and
   an illumination layer, wherein the illumination layer is manufactured via an injection molding method.

2. The x-ray detector of claim 1, wherein the electrode further includes a carrier protection layer arranged between the electrically-conductive high-voltage layer and the illumination layer.

3. The x-ray detector of claim 1, wherein the electrode further includes a second intermediate layer arranged between the electrically-conductive high-voltage layer and the illumination layer.

4. The x-ray detector of claim 1, further comprising a continuation of the electrically-conductive high-voltage layer as an electrically-conductive connection to a voltage source.

5. The x-ray detector of claim 1, further including a light source for coupling a quantity of light into the illumination layer.

6. The x-ray detector of claim 1, wherein a quantity of light coupled in from the illumination layer by way of a coupling-out structure onto the converter element varies by less then 50 percent within an illuminated surface of the converter element.

7. The x-ray detector of claim 1, wherein the electrode absorbs less than 30 percent of the x-ray radiation irradiated into the converter element.

8. A detector module comprising at least one of the x-ray detector of claim 1.

9. The detector module of claim 8, wherein the at least one of the x-ray detector includes a plurality of x-ray detectors and wherein the illumination layer is assigned to at least two of the plurality of x-ray detectors.

10. The detector module of claim 8, wherein the at least one of the x-ray detector includes a plurality of x-ray detectors and wherein at least two of the plurality of x-ray detectors are arranged at an angle in relation to one another.

11. A medical device comprising the x-ray detector of claim 1.

12. A medical device comprising the detector module of claim 8.

13. A method for manufacturing a counting x-ray detector, comprising:
   providing a flowable mold material and a converter element with attached contact layer;
   injection molding the mold material to manufacture an illumination layer;
   attaching a high-voltage layer to the illumination layer; and
   electrically-conductively connecting the high-voltage layer to the contact layer.

14. A detector module comprising at least one of the x-ray detector of claim 2.

15. The detector module of claim 14, wherein the at least one of the x-ray detector includes a plurality of x-ray detectors and wherein the illumination layer is assigned to at least two of the plurality of x-ray detectors.

16. The detector module of claim 14, wherein the at least one of the x-ray detector includes a plurality of x-ray detectors and wherein at least two of the plurality of x-ray detectors are arranged at an angle in relation to one another.

17. The detector module of claim 9, wherein the at least one of the x-ray detector includes a plurality of x-ray detectors and wherein at least two of the plurality of x-ray detectors are arranged at an angle in relation to one another.

18. A medical device comprising the x-ray detector of claim 2.

19. A medical device comprising the detector module of claim 9.

* * * * *